United States Patent [19]

Nakamine et al.

[11] Patent Number: 4,983,493

[45] Date of Patent: Jan. 8, 1991

[54] DYES FOR HEAT SENSITIVE TRANSFER RECORDING

[75] Inventors: Takeshi Nakamine; Michio Ono; Seiiti Kubodera, all of Kanagawa, Japan

[73] Assignee: Fuji Photo Film Co., Ltd., Kanagawa, Japan

[21] Appl. No.: 218,789

[22] Filed: Jul. 14, 1988

[30] Foreign Application Priority Data

Jul. 15, 1987 [JP] Japan ................................ 62-176625

[51] Int. Cl.$^5$ ........................ G03C 8/00; C07D 279/36; C07D 471/00; C07D 217/22

[52] U.S. Cl. ........................................ 430/201; 544/31; 546/81; 546/141; 546/143; 546/157; 546/158

[58] Field of Search ............... 546/157, 158, 141, 143, 546/81; 544/31; 430/201

[56] References Cited

U.S. PATENT DOCUMENTS

| | | | |
|---|---|---|---|
| 2,754,293 | 7/1956 | Brody et al. | 546/157 |
| 4,695,287 | 9/1987 | Evans et al. | 8/471 |

FOREIGN PATENT DOCUMENTS

| | | |
|---|---|---|
| 63-104050 | 5/1988 | Japan . |
| 2161824 | 1/1986 | United Kingdom . |

OTHER PUBLICATIONS

Cooper, Spectroscopic Techniques for Organic Chemists (New York, J. Wiley & Co. 1980), pp. 240–243.
Shiba et al., "Color Photo Sect Print", Chem. Abs., vol. 110, No. 4, Entry 110:31446u (1989).

*Primary Examiner*—Mukund J. Shah
*Assistant Examiner*—E. G. Ward
*Attorney, Agent, or Firm*—Sughrue, Mion, Zinn, MacPeak & Seas

[57] ABSTRACT

A dye for heat sensitive transfer recording represented by formula (I):

(I)

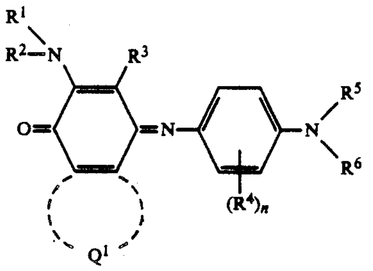

wherein $Q^1$ represents an atomic group, which includes at least one nitrogen atom, which is required, together with the carbon atoms to which said atomic group is bonded, to form an at least five membered nitrogen containing heterocyclic ring; $R_1$ represents an acyl group or a sulfonyl group; $R_2$ represents a hydrogen atom or an aliphatic group which has from 1 to 6 carbon atoms; $R_3$ represents a hydrogen atom, a halogen atom, an alkoxy group, or an aliphatic group which has from 1 to 6 carbon atoms; $R_4$ represents a halogen atom, an alkoxy group, or an aliphatic group which has from 1 to 6 carbon atoms; n represents an integer of from 0 to 4; $R_3$ may be joined to $R^1$, $R^2$, or $R^4$ to form a ring; $R^5$ and $R^6$, which may be the same or different, each represents a hydrogen atom, an aliphatic group which has from 1 to 6 carbon atoms, or an aromatic group; $R^5$ and $R^6$ may be joined together to form a ring; and at least one of $R^5$ and $R^6$ may be joined with $R^4$ to form a ring.

3 Claims, No Drawings

DYES FOR HEAT SENSITIVE TRANSFER RECORDING

FIELD OF THE INVENTION

This invention relates to dyes for heat sensitive transfer recording purposes.

BACKGROUND OF THE INVENTION

In the past there has been a demand for techniques by which facsimile printers, copiers and television images etc. can be recorded in color. Color recording techniques using electrophotography, ink jets and heat sensitive transfer etc. have been investigated for this purpose.

The heat sensitive copy recording system is such that the equipment is easy to maintain and operate, and the equipment and consumables therefor are cheap. Thus, it is thought to have an advantage over the other methods listed above.

Heat sensitive copying systems include (1) fusion systems which employ a transfer sheet, in which a layer of ink which can be melted by heating is formed on a base film, is heated using a heat sensitive head so that the ink is melted and a copy is recorded on the object on which the recording is to be made; and (2) sublimation systems which employ a transfer sheet, in which an ink layer which contains a sublimable dye has been formed on a base film, is heated by a heat sensitive head so that the dye sublimes and a copy is recorded on the object on which the recording is to be made. It is possible to control the extent of the sublimation of the dye by varying the energy which is supplied to the heat sensitive head in the case of the sublimation system. Thus, with this method, it is easy to achieve graded recording, a particular advantage for full color recording.

Dyes which are to be used in such a recording system must satisfy the following conditions: (1) the dyes must sublime easily under the operation conditions of the heat sensitive recording head, (2) the dyes must not be thermally degraded under the operating conditions of the heat sensitive recording head, (3) the dyes must have the hue preferred from the point of view of color reproduction, (4) the dyes must have a large molar extinction coefficient and be stable with respect to heat, light, humidity and chemicals etc., (5) the dyes must be easily prepared, and (6) the dyes must be suitable as inks, etc.

The dyes which have been suggested in the past, for example the anthraquinone dyes, naphthoquinone dyes etc. disclosed in JP-A-60-151097 and JP-A-60-151098 etc. have a poor hue, and the indoaniline dyes disclosed in JP-A-61-22993 have the disadvantage of poor heat resistance and light resistance. (The term "JP-A" used herein means an "unexamined published Japanese patent application".)

SUMMARY OF THE INVENTION

An object of this invention is to provide cyan dyes for heat sensitive transfer recording which satisfy the above mentioned requirements.

The other objects and effects of this invention will be apparent from the following description.

The above objects of this invention has been realized by a dye for heat sensitive transfer recording represented by formula (I):

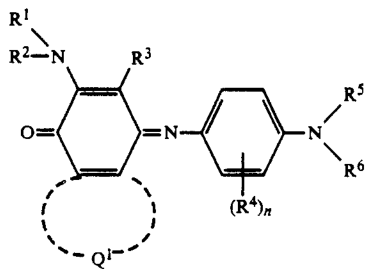

(I)

wherein $Q^1$ represents an atomic group, which includes at least one nitrogen atom, which is required, together with the carbon atoms to which said atomic group is bonded, to form an at least five membered nitrogen containing heterocyclic ring; $R_1$ represents an acyl group or a sulfonyl group; $R_2$ represents a hydrogen atom or an aliphatic group which has from 1 to 6 carbon atoms; $R_3$ represents a hydrogen atom, a halogen atom, an alkoxy group, or an aliphatic group which has from 1 to 6 carbon atoms; $R_4$ represents a halogen atom, an alkoxy group, or an aliphatic group which has from 1 to 6 carbon atoms; n represents an integer of from 0 to 4; $R_3$ may be joined to $R^1$, $R^2$, or $R^4$ to form a ring; $R^5$ and $R_6$, which may be the same or different, each represents a hydrogen atom, an aliphatic group which has from 1 to 6 carbon atoms, or an aromatic group; $R^5$ and $R^6$ may be joined together to form a ring; and at least one of $R^5$ and $R^6$ may be joined with $R^4$ to form a ring.

DETAILED DESCRIPTION OF THE INVENTION

Formula (I) is described in more detail below.

$Q^1$ represents a group of atoms, which includes at least one nitrogen atom, which is required, along with the carbon atoms to which it is bonded, to form an at least five membered nitrogen containing heterocyclic ring. Examples of divalent groups, excluding the said nitrogen atom, from which the ring can be formed include divalent amino groups, ether bonds, thioether bonds, alkylene groups, vinylene groups, imino groups, sulfonyl groups, carbonyl groups, arylene groups, divalent heterocyclic groups etc, and groups in which a plurality of these groups are combined. Moreover, these groups may have substituent groups such as alkyl groups, aryl groups, alkoxy groups and halogen atoms.

$Q^1$ preferably represents the groups

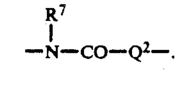

Examples of $Q^2$ include divalent amino groups, ether bonds, thioether bonds, alkylene groups, ethylene bonds, imino bonds, sulfonyl groups, carbonyl groups, arylene groups, divalent heterocyclic groups and groups consisting of combinations of such groups.

$R^7$ is a hydrogen atom or a group which can be substituted on a nitrogen atom and which can be represented by $-X^1-R^8$, where $X^1$ represents a simple bond or a divalent linking group. Examples of such divalent linking groups include divalent amino groups, ether bonds, thioether bonds, alkylene groups, ethylene bonds, imino bonds, sulfonyl groups, sulfoxy groups, carbonyl groups etc., and it may be a group consisting of a combination of these groups. Moreover, these groups may have substituent groups.

$R^8$ represents a chain-like or cyclic aliphatic group which preferably has from 1 to 6 carbon atoms (for example, methyl, butyl, cyclohexyl), an aryl group (for example, phenyl), or a heterocyclic group (for example, 2-pyridyl, 2-imidazolyl, 2-furyl), and these groups may be substituted with at least one group selected from among alkyl groups, aryl groups, heterocyclic groups, alkoxy groups (for example, methoxy, 2-methoxyethoxy), aryloxy groups (for example, 2-chlorophenoxy, 4-cyanophenoxy), alkenyloxy groups (for example, 2-propenyloxy), acyl groups (for benzoyl), ester groups (for example, butoxycarbonyl, phenoxycarbonyl, acetoxy, benzoyloxy, butoxysulfonyl, toluenesulfonyloxy), amido groups (for example, acetylamido, ethylcarbamoyl, dimethylcarbamoyl, methanesulfonamido, butylsulfamoyl), sulfamido groups (for example, dipropylsulfamoylamino), imido groups (for example, succinimido, hydantoinyl), ureido groups (for example, phenylureido, dimethylureido), aliphatic or aromatic sulfonyl groups (for example, methanesulfonyl, phenylsulfonyl), aliphatic or aromatic thio groups (for example, ethylthio, phenylthio), hydroxyl groups, cyano groups, carboxyl groups, nitro groups, sulfo group, halogen atoms etc.

The above mentioned aliphatic groups may be linear chain, branched or cyclic and they may be either saturated or unsaturated.

$R^1$ is preferably a group which can be represented by $-CO-X^2-R^9$ or $-SO_2-X^2-R^9$.

$X^2$ represents $-O-$,

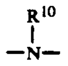

or a simple bond. $R^9$ is the same as $R^8$ described earlier. $R^9$ is preferably an alkyl group or an alkyl group of which all of the hydrogen atoms have been replaced by halogen atoms, or a phenyl group. $R^{10}$ has the same meaning as $R^2$ indicated below.

$R^2$ represents a hydrogen atom or an aliphatic group which has from 1 to 6 carbon atoms (for example, methyl, ethyl, iso-propyl, cyclohexyl, 2-ethylhexyl, allyl), and these groups may have the substituent groups permitted for $R^8$.

$R^3$ represents a hydrogen atom, a halogen atom (F, Cl, or Br), alkoxy group (for example, methoxy, ethoxy, propoxy) or an aliphatic group which has from 1 to 6 carbon atoms (for example, methyl, butyl, cyclohexyl), and these groups may have the substituent groups permitted for $R^8$.

$R^4$ has the same meaning as $R^3$ (excluding a hydrogen atom), and n is an integer of value 0 to 4. In cases where n is 2 or more, the $R^4$ groups may be the same or different.

$R^3$ may be joined to $R^1$ or $R^2$, or to $R^4$ to form a ring.

$R^5$ and $R^6$ each represents a hydrogen atom, or the same aliphatic groups or aromatic groups (aryl groups or heterocyclic groups as in the case of $R^8$) as $R^8$.

$R^5$ and $R^6$ may be joined together to form a ring. Furthermore, $R^5$, $R^6$ or both $R^5$ and $R^6$ may be joined to $R^4$ to form a ring.

The dyes represented by formula (I) which are represented by formula (II) are preferred.

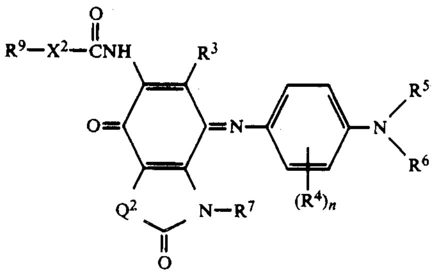

(II)

wherein $R^3$, $R^4$, $R^5$, $R^6$, $R^7$, $R^9$, $X^2$, $Q^2$, and n have the same meaning as in formula (I).

A hydrogen atom is preferred for $R^7$ in formula (II).

A group of atoms required to form a five to seven membered ring is preferred for $Q^2$ in formula (II).

A single bond is preferred for $X^2$ in formula (II).

The dyes represented by formula (I) which are represented by formula (III) are especially desirable.

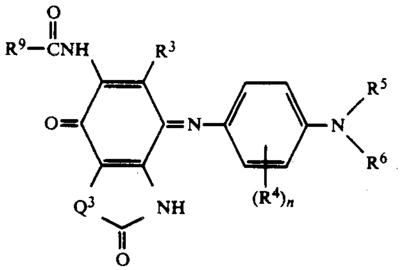

(III)

wherein $R^3$, $R^4$, $R^5$, $R^6$, $R^9$ and n are the same as in formula (II). $Q^3$ represents

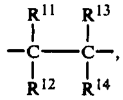, 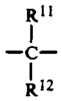, or 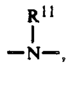, wherein $R^{11}$, $R^{12}$, $R^{13}$ and $R^{14}$ each represents a hydrogen atom or a group which can be substituted on the carbon atom or nitrogen atom (actual examples include the groups described for $R^8$ and halogen atoms).

Actual examples of these dyes and their $\lambda_{max}$ values in ethyl acetate are indicated below, but the invention is not limited to these examples.

(1)

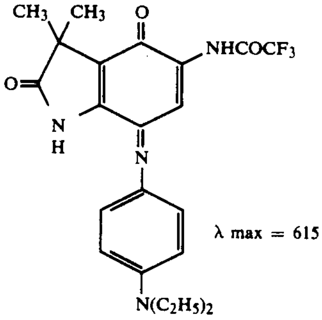

λ max = 615 nm

-continued
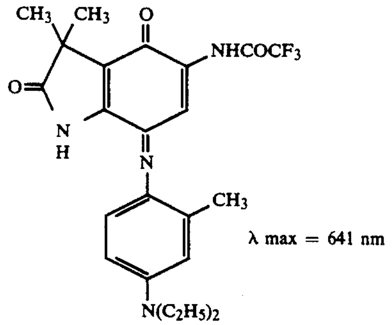
$\lambda$ max = 641 nm (2)
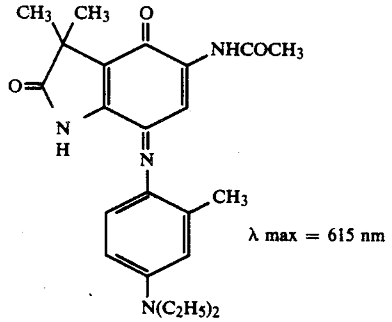
$\lambda$ max = 615 nm (3)
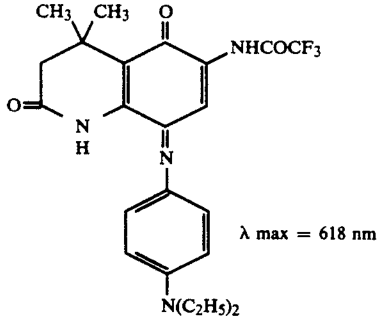
$\lambda$ max = 618 nm (4)
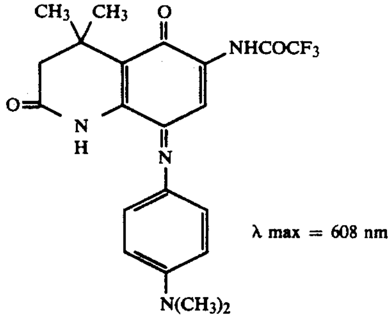
$\lambda$ max = 608 nm (5)
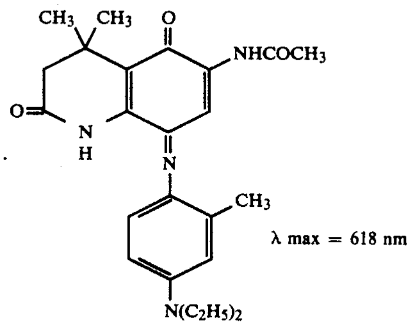
$\lambda$ max = 618 nm (6)
-continued
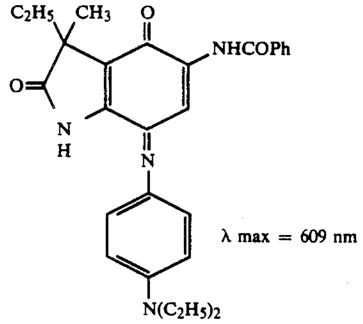
$\lambda$ max = 609 nm (7)
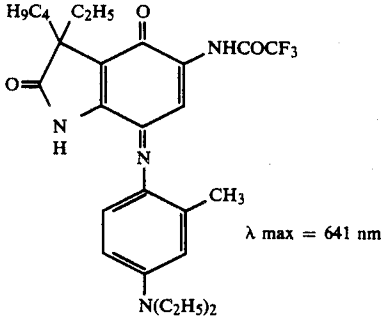
$\lambda$ max = 641 nm (8)
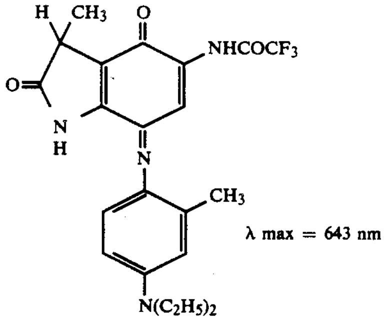
$\lambda$ max = 643 nm (9)
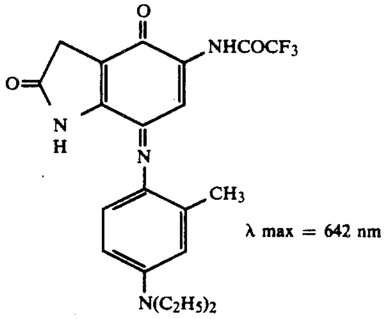
$\lambda$ max = 642 nm (10)
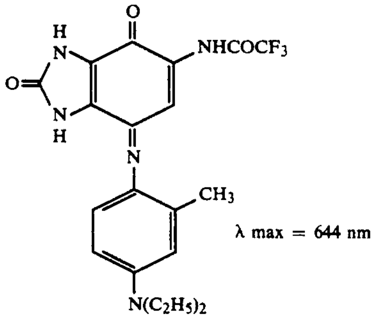
$\lambda$ max = 644 nm (11)

-continued
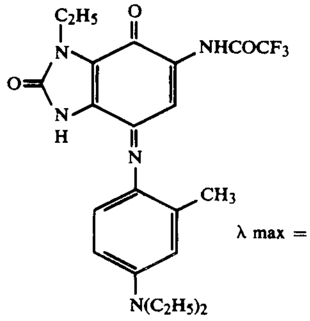
(12) λ max = 650 nm
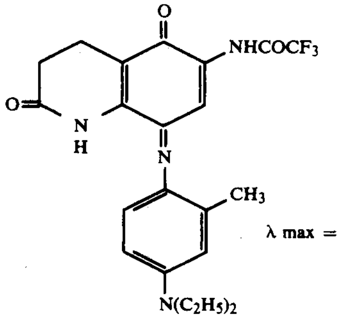
(13) λ max = 644 nm
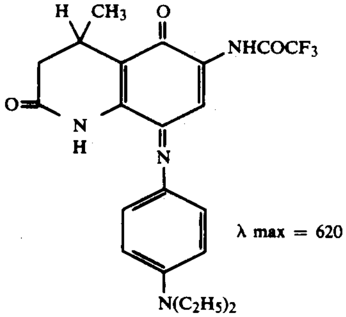
(14) λ max = 620 nm
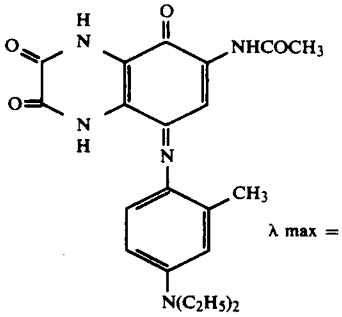
(15) λ max = 627 nm
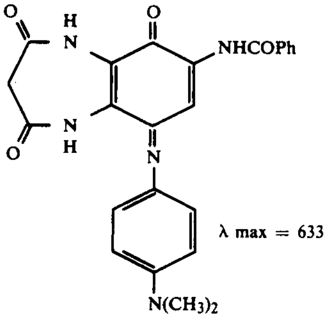
(16) λ max = 633 nm
-continued
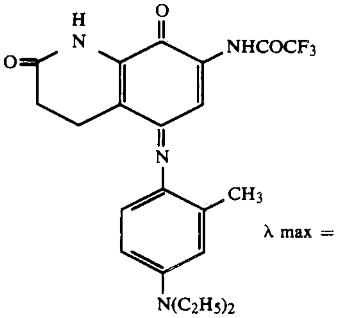
(17) λ max = 676 nm
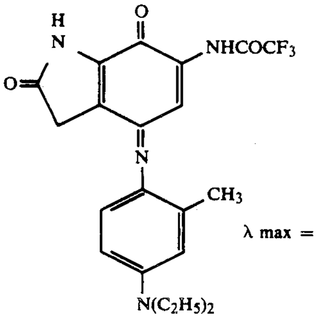
(18) λ max = 675 nm
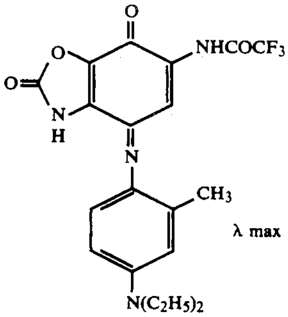
(19) λ max = 641 nm
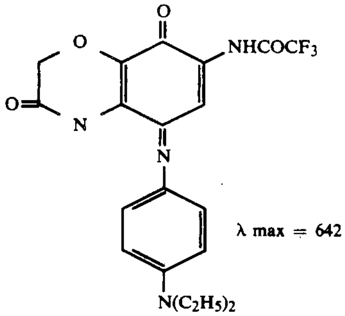
(20) λ max = 642 nm
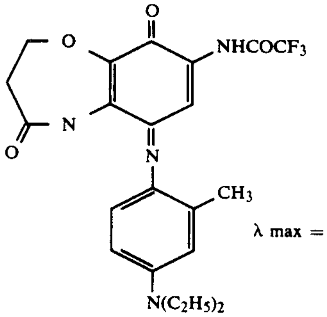
(21) λ max = 642 nm -continued
(22)
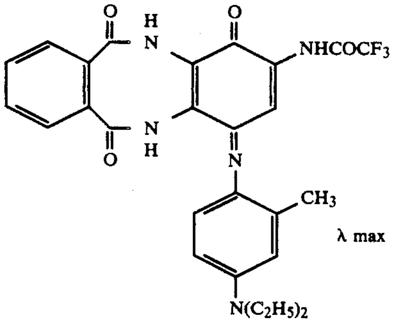
λ max = 635 nm
(23)
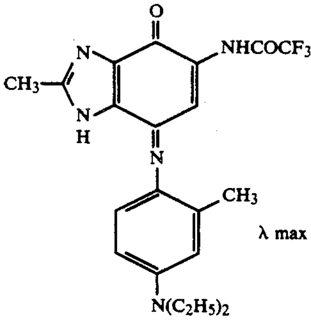
λ max = 620 nm
(24)
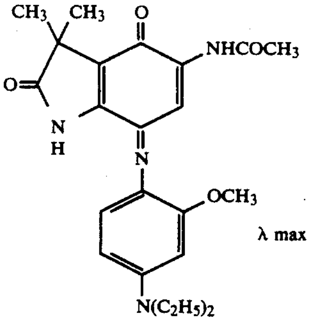
λ max = 620 nm
(25)
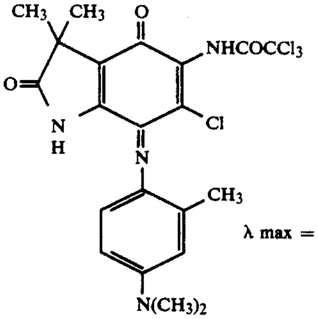
λ max = 647 nm
(26)
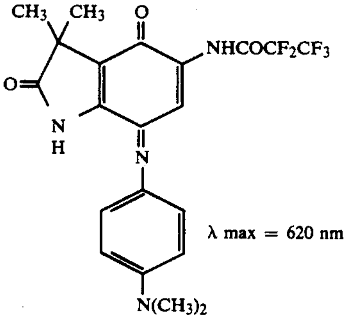
λ max = 620 nm
-continued
(27)
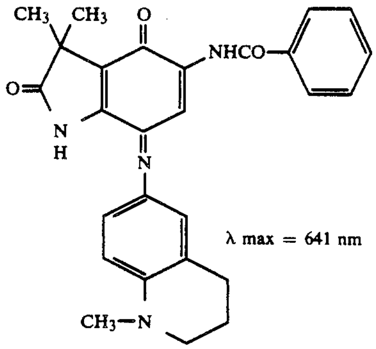
λ max = 641 nm
(28)
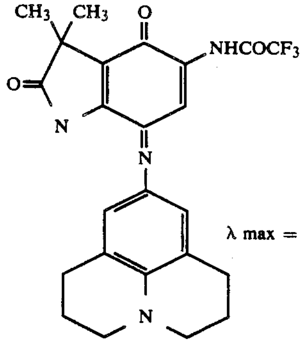
λ max = 658 nm
(29)
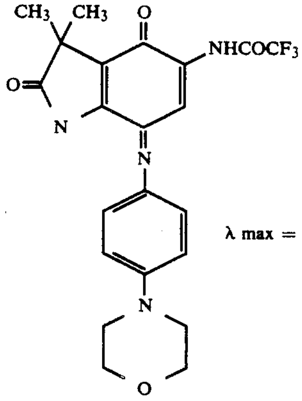
λ max = 618 nm
(30)
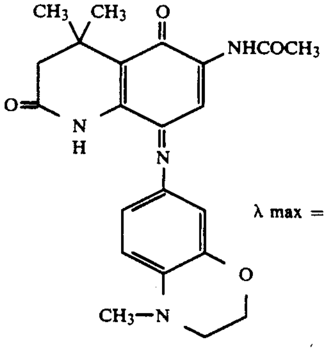
λ max = 630 nm -continued
(31)
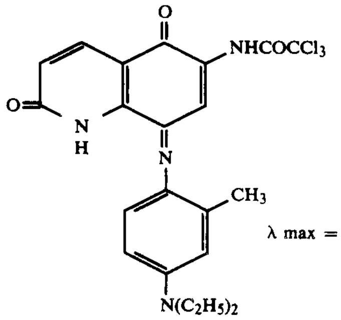
λ max = 642 nm
(32)
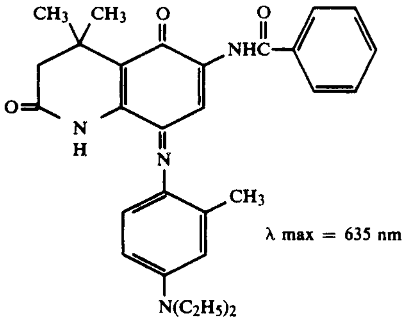
λ max = 635 nm
(33)
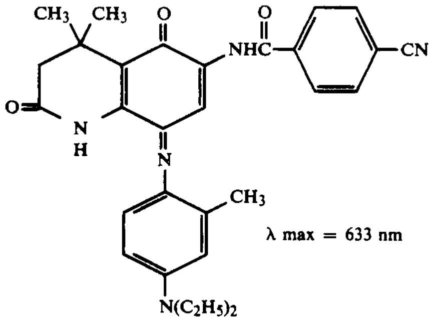
λ max = 633 nm
(34)
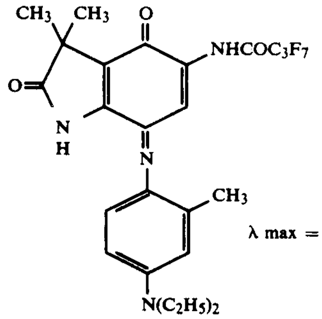
λ max = 654 nm
(35)
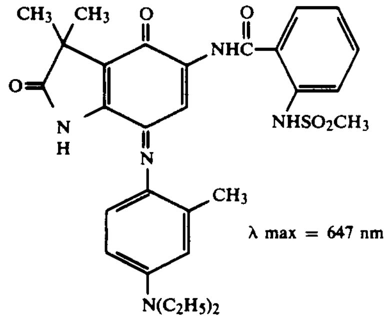
λ max = 647 nm
-continued
(36)
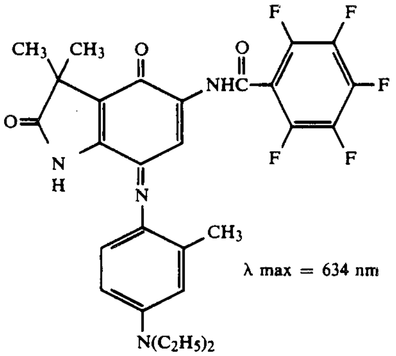
λ max = 634 nm
(37)
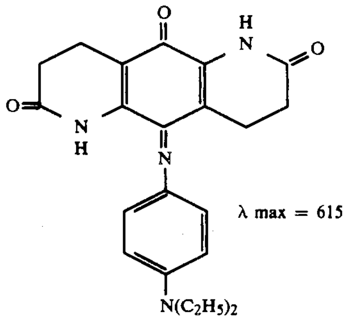
λ max = 615 nm
(38)
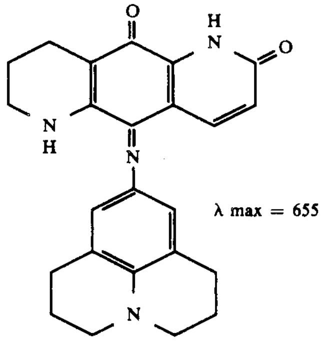
λ max = 655 nm
(39)
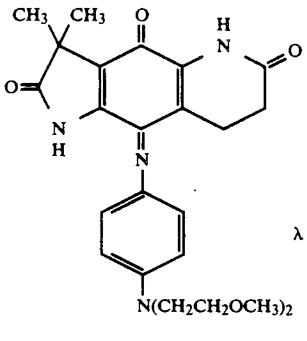
λ max = 620 nm
(40)
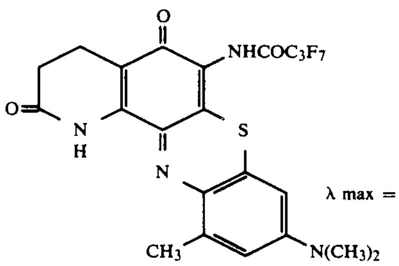
λ max = 610 nm -continued (41)

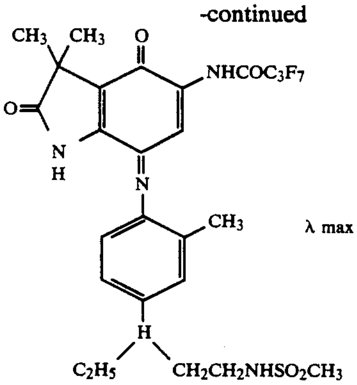

λ max = 646 nm

The above mentioned dyes of this invention can be prepared for example by acylating the amino group of compound represented by formula (IV) below and carrying out an oxidative coupling reaction using ammonium persulfate for example with a compound represented by formula (V) as disclosed in JP-A-62-29572.

(IV)

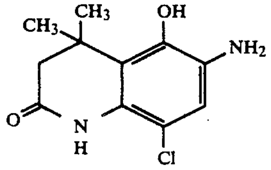

(V)

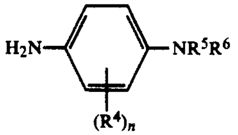

wherein $R^4$, $R^5$, $R^6$ and n have the same meaning as in formula (I).

When the compounds (dyes) of this invention are used in a heat sensitive transfer recording system, they must be formed into an ink by dissolution or dispersion in the form of fine particles (preferably having an average particle size of about 3 μm or less, and more preferably 0.5 μm or less), together with a binder, in a medium. Further, the ink must be coated onto a base film to provide a dry transfer sheet. The coated amount of the ink is preferably in the range of from about 1 to 500 $cc/m^2$, and more preferably from 5 to 200 $cc/m^2$.

Water soluble resins such as cellulose based resins, acrylic acid based resins, starch based resins etc., acrylic resins, methacrylic resins, and resins which are soluble in organic solvents, such as polystyrenes, polycarbonates, polysulfones, polyethersulfones, ethylcellulose etc., can be used as the binder, for preparing the ink. The organic solvent soluble resins can be used not only in the form of organic solvent solution but also in the form of aqueous dispersions. The amount of the binder used is preferably from about 50 to 600 parts by weight per 100 parts by weight of the compound of this invention.

Apart from water, alcohols such as methyl alcohol, isopropyl alcohol, isobutyl alcohol, etc., cellosolves such as methylcellosolve, ethylcellosolve etc., aromatics such as toluene, xylene, chlorobenzene, etc., esters such as ethyl acetate, butyl acetate etc., ketones such as acetone, methyl ethyl ketone, methyl isobutyl ketone, cyclohexanone etc., chlorinated solvents such as methylene chloride, chloroform, trichloroethylene etc, ethers such as tetrahydrofuran, dioxan etc., and organic solvents such as N,N-dimethylformamide, N-methylpyrrolidone etc., can be used as the medium when preparing an ink. The amount of the medium used is preferably from about 5 times to 100 times by weight the total amount of the compound of this invention and the binder.

The base film on which the ink is coated for preparing a transfer sheet may be a thin leaf paper, such as condenser paper or glassing paper, or a plastic film which has good heat resitance, such as a film of polyester, polyamide or polyimide, and the thickness of the base film may be within the range from 3 to 50 μm.

The ink can be coated onto the base film using a reverse roll coater, gravure coater, rod coater, air doctor coater etc.

The dyes represented by formula (I) of this invention have a bright cyan color and so they are suitable, in combination with the appropriate magenta colors and yellow colors, for obtaining full color recordings with good color reproduction. Moreover, the dyes of this invention sublime readily and have large molar extinction coefficients so that they do not impose a heavy burden on the heat sensitive head, and high color density recordings can be obtained at high speed. Moreover, these dyes are stable with respect to heat, light, humidity and chemicals etc. Thus, they are not thermally degraded during transfer recording and the storage properties of the recordings obtained are excellent. Furthermore, the dyes of this invention have good solubility in organic solvents and dispersibility in water so that highly concentrated inks in which the dyes are dissolved or dispersed uniformly can be prepared easily, and transfer sheets on which the dye has been coated uniformly at a high concentration can be obtained. Hence, it is possible by using these transfer sheets to obtain recordings which have good uniformity and color density.

This invention is described in practical terms by means of examples below, but the invention is not limited by these examples.

EXAMPLE 1

(a) Synthesis of Compound (5)

8.3 g of Compound (i) below and 3.3 g of Compound (ii) below were dissolved in 180 ml of ethyl alcohol and an aqueous solution obtained by dissolving 30 g of sodium carbonate in 180 ml of water was added. An aqueous solution obtained by dissolving 6.1 g of ammonium persulfate in 50 ml of water was then added dropwise at room temperature and reacted for a period of 1 hour. Water was added after the reaction had been completed, and the crystals which precipitated out were recovered by filtration and recrystallized from isopropyl alcohol. As a result, a refined dye represented by formula (iii) below (i.e., Compound (5) listed hereinabove) was obtained. The peak absorption wavelength of this dye (methanol) was 616 nm.

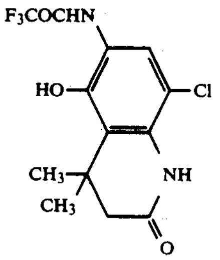

Compound (i)

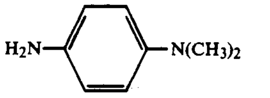

Compound (ii)

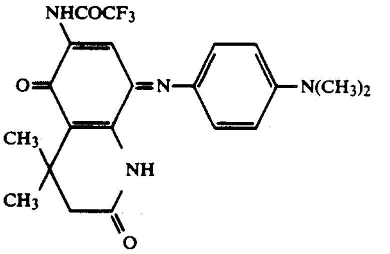

Compound (iii)

(b) Preparation of an Ink

Dye prepared in (a) above 2 g
Ethylcellulose 2 g
Isopropyl alcohol 96 g

A mixture of the composition indicated above was treated for 30 minutes in an ultra-disperser to prepare an ink.

(c) Preparation of a Transfer Sheet

The above mentioned ink was coated onto a polyethyleneterephthalate film (thickness 7 $\mu m$) using a wire bar #40 and a transfer sheet was obtained by allowing the ink to dry naturally. The coated amount of the ink was about 70 cc/$m^2$.

(d) Transfer Recording

The ink-coated surface of the above mentioned transfer sheet was placed on a top quality paper of which the surface had been coated with a polyester resin. A recording was made by heating the side of the transfer sheet opposite to the ink coated surface under the conditions indicated below. The heating was carried out using a heat sensitive head. It was possible in this way to obtain a recording in a bright cyan color having a uniform high density of 1.15.

| Recording Conditions | |
|---|---|
| Main scan, subsidiary scan line density | 4 dots/mm |
| Recording power | 1 w/dot |
| Head heating time | 5 ms |

EXAMPLE 2

An ink was prepared in the same way as in Example 1 except that Compound (2) (peak absorption wavelength (methanol) 640 nm) was used in place of the dye used in Example 1. A transfer sheet was prepared in the same way as in Example 1 and when a transfer recording was made in the same way as before a bright cyan recording having a color density of 1.10 was obtained.

EXAMPLE 3

In order to carry out light fastness tests of the recordings obtained in Examples 1 and 2, the copied sheets were exposed to light for 48 hours in a xenon lamp weatherometer (made by the U.S. Atlas Co.). Furthermore, 7 day forced heating tests were carried out at 60° C. and the extent of fading was measured in order to observe the heat resistance of the recordings obtained. The results obtained are shown in Table 1 below, along with data obtained using Comparative Dye (A) indicated below for comparison with the dyes of this invention which are indicated in Table 1 as actual examples.

Comparative Dye (A)

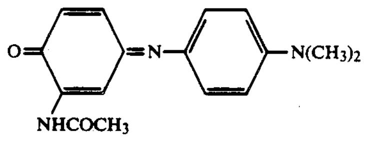

TABLE 1

| Dye | Extent of Fading in Light | Extent of Fading on Heating |
|---|---|---|
| Comparative Dye (A) | 80% | 30% |
| Compound (5) | 10% | 5% |
| Compound (2) | 10% | ca. 0% |
| Compound (3) | <10% | ca. 0% |

It is clear from these results in the above Table 1 that the dyes of this invention have considerably better light resistance and heat resistance than the known indoaniline dye used for heat sensitive transfer recording.

While the invention has been described in detail and with reference to specific embodiments thereof, it will be apparent to one skilled in the art that various changes and modifications can be made therein without departing from the spirit and scope thereof.

What is claimed is:

1. A dye for heat transfer recording represented by formula (III):

(III)

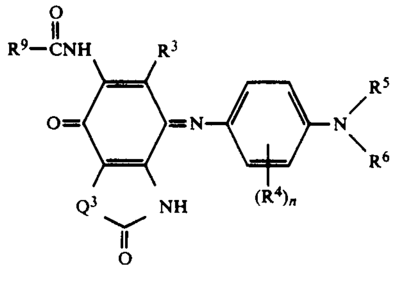

wherein $R^3$ represents a hydrogen atom, a halogen atom, an alkoxy group, or an aliphatic group which has from 1 to 6 carbon atoms; $R^4$ represents a halogen atom, an alkoxy group, or an aliphatic group which has from 1 to 6 carbon atoms; n represents an integer of from 0 to 4; $R^3$ may be joined to $R^9$ or $R^4$ to form a ring; $R^5$ and $R^6$, which may be the same or different, each represents a hydrogen atom, an aliphatic group which has from 1 to 6 carbon atoms, or a phenyl, 2-pyridyl, 2-imidazoyl or 2-furyl group; $R^5$ and $R^6$ may be joined together to form a ring; and at least one of $R^5$ and $R^6$ may be joined with $R^4$ to form a ring, $R^9$ represents a branched or straight chained or cyclic aliphatic group, an aryl group or a heterocyclic group, and wherein $Q^3$ represents —C=C—,

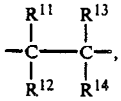, 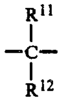 or 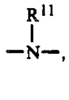, wherein $R^{11}$, $R^{12}$, $R^{13}$ and $R^{14}$ each represents a hydrogen atom or a branched or straight chained or cyclic aliphatic group.

2. A dye as claimed in claim 1, wherein at least one of $R^{11}$, $R^{12}$, $R^{13}$ and $R^{14}$, which are not hydrogen, are substituted with at least one group selected from among alkyl groups, aryl groups, heterocyclic groups, alkoxy groups, alkenyloxy groups, acyl groups, ester groups, amido groups, sulfamido groups, imido groups, ureido groups, aliphatic or aromatic sulfonyl groups, aliphatic or aromatic thio groups, hydroxyl groups, cyano group, carboxyl groups, nitro groups, sulfo group, and halogen atoms.

3. A dye as claimed in claim 1, wherein each of said branched or straight chained or cyclic aliphatic group(s) represented by $R^{11}$, $R^{12}$, $R^{13}$ and $R^{14}$ has a total carbon number of from 1 to 6.

* * * * *